(12) United States Patent
Issa et al.

(10) Patent No.: US 10,077,439 B2
(45) Date of Patent: Sep. 18, 2018

(54) REMOVAL OF DNA FRAGMENTS IN MRNA PRODUCTION PROCESS

(71) Applicant: ModernaTX, Inc., Cambridge, MA (US)

(72) Inventors: William Joseph Issa, Roslindale, MA (US); Yuxun Wang, Cambridge, MA (US); Stephane Bancel, Cambridge, MA (US)

(73) Assignee: ModernaTX, Inc., Cambridge, MA (US)

( * ) Notice: Subject to any disclaimer, the term of this patent is extended or adjusted under 35 U.S.C. 154(b) by 0 days.

(21) Appl. No.: 14/777,301

(22) PCT Filed: Mar. 13, 2014

(86) PCT No.: PCT/US2014/026838
§ 371 (c)(1),
(2) Date: Sep. 15, 2015

(87) PCT Pub. No.: WO2014/152030
PCT Pub. Date: Sep. 25, 2014

(65) Prior Publication Data
US 2016/0024492 A1 Jan. 28, 2016

Related U.S. Application Data

(60) Provisional application No. 61/799,872, filed on Mar. 15, 2013.

(51) Int. Cl.
*C12Q 1/68* (2018.01)
*C07H 21/00* (2006.01)
*C12N 15/10* (2006.01)
*C12Q 1/6806* (2018.01)

(52) U.S. Cl.
CPC ....... *C12N 15/1006* (2013.01); *C12N 15/101* (2013.01); *C12Q 1/6806* (2013.01)

(58) Field of Classification Search
CPC ....... C12Q 1/68; C07H 21/00; C12N 15/1003
See application file for complete search history.

(56) References Cited

U.S. PATENT DOCUMENTS

| | | | |
|---|---|---|---|
| 4,588,585 A | 5/1986 | Mark et al. |
| 4,699,717 A | 10/1987 | Riesner et al. |
| 4,737,462 A | 4/1988 | Mark et al. |
| 4,816,567 A | 3/1989 | Cabilly et al. |
| 4,959,314 A | 9/1990 | Mark et al. |
| 5,057,426 A | 10/1991 | Henco et al. |
| 5,489,677 A | 2/1996 | Sanghvi et al. |
| 5,591,722 A | 1/1997 | Montgomery et al. |
| 5,599,667 A | 2/1997 | Arnold, Jr. et al. |
| 5,637,459 A | 6/1997 | Burke et al. |
| 5,639,873 A | 6/1997 | Barascut et al. |
| 5,789,578 A | 8/1998 | Burton et al. |
| 6,011,148 A | 1/2000 | Bussey et al. |
| 6,248,268 B1 | 6/2001 | Cook |
| 6,423,492 B1 | 7/2002 | Harbron |
| 6,511,832 B1 | 1/2003 | Guarino et al. |
| 6,881,314 B1 | 4/2005 | Wang et al. |
| 7,691,569 B2 | 4/2010 | Wohlgemuth et al. |
| 7,745,391 B2 | 6/2010 | Mintz et al. |
| 8,093,367 B2 | 1/2012 | Kore et al. |
| 8,664,194 B2 | 3/2014 | de Fougerolles et al. |
| 8,680,069 B2 | 3/2014 | de Fougerolles et al. |
| 8,710,200 B2 | 4/2014 | Schrum et al. |
| 8,822,663 B2 | 9/2014 | Schrum et al. |
| 8,898,864 B1 | 12/2014 | Porter |
| 8,980,864 B2 | 3/2015 | Hoge et al. |
| 8,999,380 B2 | 4/2015 | Bancel et al. |

(Continued)

FOREIGN PATENT DOCUMENTS

| | | |
|---|---|---|
| CA | 2028849 A1 | 9/1991 |
| CA | 2473135 A1 | 6/2003 |

(Continued)

OTHER PUBLICATIONS

Crain, "Preparation and enzymatic hydrolysis of DNA and RNA for mass spectrometry," Methods in Enzymology, 193:782-790, 1990. Cited by third Party under 37 CFR 1.290.*

Krieg et al., Functional messenger RNA are produced by SP6 in vitro transcription of cloned cDNAs. Nucleic Acids Research 12(18) : 7057 (1984).*

Liu et al., "In vitro Transcription on DNA Templates Immobilized to Streptavidin MagneSphere(r) Paramagnetic Particles," Promega Notes, No. 64 : 21(1997). Cited by third Party under 37 CFR 1.290.*

Melton et al., Efficient in vitro synthesis of biologically active RNA and RNA hybridization probes from plasmids containing a bacteriophage SP6 promoter. Nucleic Acids Research 12(18) : 7035 (1984).*

Pomerantz and McCloskey, "Analysis of RNA Hydrolyzates by liquid chromatography-mass spectrometry," Methods in Enzymology, 193:796(1990). Cited by third Party under 37 CFR 1.290.*

(Continued)

*Primary Examiner* — Ethan C Whisenant
(74) *Attorney, Agent, or Firm* — Clark & Elbing LLP

(57) ABSTRACT

The present invention describes methods of removing DNA from an RNA transcript during the mRNA production process. The method embodies procedures for obtaining an in vitro transcription product, and removing any DNA from the product. The DNA can be removed by adding either free DNase or a resin containing immobilized DNase to the product, and recovering the RNA transcript. Alternatively, the DNA template used in the in vitro transcription reaction is labeled. After transcription, the product is applied to a resin that is configured to bind the label, and the RNA transcript is recovered. To detect whether any residual impurities are left in the RNA transcript product, the product is subjected to nuclease digestion and subsequently to liquid chromatography-tandem mass spectrometry analysis to quantitate any residual DNA. The present invention demonstrates efficient and effective methods of isolating an RNA transcript from an in vitro transcription product.

11 Claims, 1 Drawing Sheet
Specification includes a Sequence Listing.

(56) References Cited

U.S. PATENT DOCUMENTS

| | | |
|---|---|---|
| 9,050,297 B2 | 6/2015 | Chakraborty et al. |
| 9,061,059 B2 | 6/2015 | Chakraborty et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,149,506 B2 | 10/2015 | Chakraborty et al. |
| 9,428,535 B2 | 8/2016 | de Fougerolles et al. |
| 2001/0025097 A1* | 9/2001 | Sheridan ............... A61K 31/70 530/311 |
| 2002/0001812 A1 | 1/2002 | Smith et al. |
| 2002/0016450 A1 | 2/2002 | Laugharn et al. |
| 2002/0058256 A1 | 5/2002 | Rothberg et al. |
| 2002/0114784 A1* | 8/2002 | Li ....................... C12N 15/113 424/93.2 |
| 2002/0153312 A1 | 10/2002 | Gjerde et al. |
| 2003/0120065 A1 | 6/2003 | Froehler et al. |
| 2003/0138419 A1 | 7/2003 | Radic et al. |
| 2003/0170810 A1 | 9/2003 | Vedadi et al. |
| 2003/0180779 A1 | 9/2003 | Lofton-Day et al. |
| 2004/0038278 A1 | 2/2004 | Tzertzinis et al. |
| 2004/0076978 A1* | 4/2004 | Verfaillie ............. C12Q 1/6886 435/6.11 |
| 2004/0142433 A1* | 7/2004 | Padgett ............. C12N 15/1027 435/91.2 |
| 2004/0220127 A1 | 11/2004 | Sternberg et al. |
| 2004/0224425 A1 | 11/2004 | Gjerde et al. |
| 2004/0259097 A1 | 12/2004 | De Backer et al. |
| 2005/0003496 A1 | 1/2005 | McGall et al. |
| 2005/0053942 A1 | 3/2005 | Kauppinen et al. |
| 2005/0130196 A1 | 6/2005 | Hofstadler et al. |
| 2005/0171333 A1* | 8/2005 | Paulsen ................ C07H 21/00 530/300 |
| 2006/0003371 A1 | 1/2006 | Russell et al. |
| 2006/0223081 A1 | 10/2006 | Jarrell et al. |
| 2007/0020678 A1 | 1/2007 | Ault-Riche et al. |
| 2007/0281336 A1 | 12/2007 | Jendrisak et al. |
| 2008/0076910 A1 | 3/2008 | Takkellapati et al. |
| 2008/0153078 A1 | 6/2008 | Braman et al. |
| 2008/0171711 A1* | 7/2008 | Hoerr .................. A61K 9/0019 514/44 R |
| 2009/0099041 A1 | 4/2009 | Church et al. |
| 2009/0192303 A1 | 7/2009 | Skagestad |
| 2009/0286852 A1 | 11/2009 | Kariko et al. |
| 2010/0047261 A1 | 2/2010 | Hoerr et al. |
| 2010/0048883 A1 | 2/2010 | Ketterer et al. |
| 2010/0178272 A1* | 7/2010 | Hartmann .......... A61K 31/7105 424/85.4 |
| 2010/0189729 A1 | 7/2010 | Hoerr et al. |
| 2010/0317532 A1 | 12/2010 | Liu et al. |
| 2011/0143397 A1 | 6/2011 | Kariko et al. |
| 2011/0218170 A1 | 9/2011 | Thottassery et al. |
| 2011/0250225 A1* | 10/2011 | Fotin-Mleczek ......................... A61K 39/0011 424/193.1 |
| 2011/0294205 A1 | 12/2011 | Hukari et al. |
| 2011/0319506 A1 | 12/2011 | Erbacher et al. |
| 2012/0046346 A1 | 2/2012 | Rossi et al. |
| 2012/0100136 A1 | 4/2012 | Patel et al. |
| 2012/0140097 A1 | 6/2012 | Morita et al. |
| 2012/0251618 A1 | 10/2012 | Schrum et al. |
| 2013/0052721 A1 | 2/2013 | Hollander et al. |
| 2013/0115272 A1 | 5/2013 | de Fougerolles et al. |
| 2013/0123481 A1 | 5/2013 | de Fougerolles et al. |
| 2013/0156849 A1 | 6/2013 | de Fougerolles et al. |
| 2013/0165504 A1 | 6/2013 | Bancel et al. |
| 2013/0203115 A1 | 8/2013 | Schrum et al. |
| 2013/0244282 A1 | 9/2013 | Schrum et al. |
| 2013/0245103 A1 | 9/2013 | de Fougerolles et al. |
| 2013/0245106 A1 | 9/2013 | de Fougerolles et al. |
| 2013/0251618 A1 | 9/2013 | Li et al. |
| 2013/0259923 A1 | 10/2013 | Bancel et al. |
| 2013/0259924 A1 | 10/2013 | Bancel et al. |
| 2014/0010861 A1 | 1/2014 | Bancel et al. |
| 2014/0105964 A1 | 4/2014 | Bancel et al. |
| 2014/0105966 A1 | 4/2014 | Bancel et al. |
| 2014/0147454 A1 | 5/2014 | Chakraborty et al. |
| 2014/0200261 A1 | 7/2014 | Hoge et al. |
| 2014/0206752 A1 | 7/2014 | Afeyan et al. |
| 2014/0206852 A1 | 7/2014 | Hoge et al. |
| 2014/0241956 A1 | 8/2014 | Page et al. |
| 2014/0243399 A1 | 8/2014 | Schrum et al. |
| 2014/0275227 A1 | 9/2014 | Hoge et al. |
| 2014/0343129 A1 | 11/2014 | de Fougerolles et al. |
| 2015/0005372 A1 | 1/2015 | Hoge et al. |
| 2015/0017211 A1 | 1/2015 | de Fougerolles et al. |
| 2015/0030576 A1 | 1/2015 | Bancel |
| 2015/0044758 A1 | 2/2015 | Amshey et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064725 A1 | 3/2015 | Schrum et al. |
| 2015/0086614 A1 | 3/2015 | Bancel et al. |
| 2015/0111248 A1 | 4/2015 | Bancel et al. |
| 2015/0141499 A1 | 5/2015 | Bancel et al. |
| 2015/0157781 A1 | 6/2015 | Kyle et al. |
| 2015/0166616 A1 | 6/2015 | Bancel et al. |
| 2015/0167017 A1 | 6/2015 | Roy et al. |
| 2015/0211039 A1 | 7/2015 | Wang et al. |
| 2015/0307542 A1 | 10/2015 | Roy et al. |
| 2016/0017313 A1 | 1/2016 | Spivak et al. |
| 2016/0024140 A1 | 1/2016 | Issa et al. |
| 2016/0024141 A1 | 1/2016 | Issa et al. |
| 2016/0024492 A1 | 1/2016 | Issa et al. |
| 2016/0024547 A1 | 1/2016 | Bancel et al. |
| 2016/0032273 A1 | 2/2016 | Shahrokh et al. |
| 2016/0038612 A1 | 2/2016 | Hoge et al. |
| 2016/0040154 A1 | 2/2016 | Heartlein et al. |
| 2016/0177295 A1 | 6/2016 | Rudolph et al. |
| 2016/0194368 A1 | 7/2016 | Hoge et al. |
| 2016/0194625 A1 | 7/2016 | Hoge et al. |
| 2016/0237108 A1 | 8/2016 | Fraley et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354492 A1 | 12/2016 | Roy et al. |
| 2017/0136131 A1 | 5/2017 | Roy et al. |
| 2017/0136132 A1 | 5/2017 | Roy et al. |
| 2017/0175129 A1 | 6/2017 | Roy et al. |

FOREIGN PATENT DOCUMENTS

| | | |
|---|---|---|
| EP | 0366400 A2 | 5/1990 |
| EP | 1083232 B1 | 2/2005 |
| EP | 1619254 A1 | 1/2006 |
| EP | 1383556 B9 | 3/2008 |
| EP | 2092064 B1 | 9/2010 |
| EP | 2377938 A1 | 10/2011 |
| EP | 2484770 A1 | 8/2012 |
| EP | 2188379 B1 | 1/2013 |
| EP | 2548960 A1 | 1/2013 |
| JP | 2008-509168 A | 3/2008 |
| WO | WO-91/05058 A1 | 4/1991 |
| WO | WO-93/03052 A1 | 2/1993 |
| WO | WO-97/07825 A1 | 3/1997 |
| WO | WO-01/55306 A2 | 8/2001 |
| WO | WO-01/81566 A2 | 11/2001 |
| WO | WO-02/44399 A2 | 6/2002 |
| WO | WO-2004/005544 A2 | 1/2004 |
| WO | WO-2004/020575 A2 | 3/2004 |
| WO | WO-2005/042716 A2 | 5/2005 |
| WO | WO-2005/058933 A1 | 6/2005 |
| WO | WO-2006/015445 A1 | 2/2006 |
| WO | WO-2007/024708 A2 | 3/2007 |
| WO | WO-2007/120863 A2 | 10/2007 |
| WO | WO-2008/045505 A2 | 4/2008 |
| WO | WO-2008/083949 A2 | 7/2008 |
| WO | WO-2009/016431 A1 | 2/2009 |
| WO | WO-2009/042971 A2 | 4/2009 |
| WO | WO-2009/127230 A1 | 10/2009 |
| WO | WO-2009/149253 A2 | 12/2009 |

(56) References Cited

FOREIGN PATENT DOCUMENTS

| | | |
|---|---|---|
| WO | WO-2010/017510 A1 | 2/2010 |
| WO | WO-2010/109289 A1 | 9/2010 |
| WO | WO-2011/012316 A2 | 2/2011 |
| WO | WO-2011/012316 A3 | 2/2011 |
| WO | WO-2011/071931 A2 | 6/2011 |
| WO | WO-2011/127933 A1 | 10/2011 |
| WO | WO-2011/133868 A2 | 10/2011 |
| WO | WO-2012/019168 A2 | 2/2012 |
| WO | WO-2012/135805 A2 | 10/2012 |
| WO | WO-2012/138530 A1 | 10/2012 |
| WO | WO-2012/158736 A1 | 11/2012 |
| WO | WO-2012/164565 A1 | 12/2012 |
| WO | WO-2013/045434 A1 | 4/2013 |
| WO | WO-2013/052523 A1 | 4/2013 |
| WO | WO-2013/063468 A1 | 5/2013 |
| WO | WO-2013/090294 A1 | 6/2013 |
| WO | WO-2013/090648 A1 | 6/2013 |
| WO | WO-2013/090897 A1 | 6/2013 |
| WO | WO-2013/096709 A2 | 6/2013 |
| WO | WO-2013/101690 A1 | 7/2013 |
| WO | WO-2013/113326 A1 | 8/2013 |
| WO | WO-2013/113501 A1 | 8/2013 |
| WO | WO-2013/113502 A1 | 8/2013 |
| WO | WO-2013/130161 A1 | 9/2013 |
| WO | WO-2013/151663 A1 | 10/2013 |
| WO | WO-2013/151665 A2 | 10/2013 |
| WO | WO-2013/151666 A2 | 10/2013 |
| WO | WO-2013/151668 A2 | 10/2013 |
| WO | WO-2013/151670 A2 | 10/2013 |
| WO | WO-2013/151672 A2 | 10/2013 |
| WO | WO-2014/028429 A2 | 2/2014 |
| WO | WO-2014/081507 A1 | 5/2014 |
| WO | WO-2014/093574 A1 | 6/2014 |
| WO | WO-2014/093924 A1 | 6/2014 |
| WO | WO-2014/113089 A2 | 7/2014 |
| WO | WO-2014/152030 A1 | 9/2014 |
| WO | WO-2014/152211 A1 | 9/2014 |
| WO | WO-2014/152513 A1 | 9/2014 |
| WO | WO-2014/152540 A1 | 9/2014 |
| WO | WO-2014/152659 A1 | 9/2014 |
| WO | WO-2014/152673 A1 | 9/2014 |
| WO | WO-2014/164253 A1 | 10/2014 |
| WO | WO-2015/006747 A2 | 1/2015 |
| WO | WO-2015/034925 A1 | 3/2015 |
| WO | WO-2015/034928 A1 | 3/2015 |
| WO | WO-2015/038892 A1 | 3/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/051214 A1 | 4/2015 |
| WO | WO-2015/058069 A1 | 4/2015 |
| WO | WO-2015/070413 A1 | 5/2015 |
| WO | WO-2015/085318 A2 | 6/2015 |
| WO | WO-2015/089511 A2 | 6/2015 |
| WO | WO-2015/101416 A1 | 7/2015 |
| WO | WO-2015/105926 A1 | 7/2015 |
| WO | WO-2015/179598 A2 | 11/2015 |
| WO | WO-2015/196118 A1 | 12/2015 |
| WO | WO-2015/196128 A2 | 12/2015 |
| WO | WO-2015/196130 A2 | 12/2015 |
| WO | WO-2016/011222 A2 | 1/2016 |
| WO | WO-2016/011226 A1 | 1/2016 |
| WO | WO-2016/034620 A1 | 3/2016 |
| WO | WO-2016/036902 A1 | 3/2016 |
| WO | WO-2016/118724 A1 | 7/2016 |
| WO | WO-2016/118725 A1 | 7/2016 |

OTHER PUBLICATIONS

R.L. St. Claire, III.Positive ion electrospray ionization tandem mass spectrometry coupled to ion-pairing highperformance liquid chromatography with a phosphate buffer for the quantitative analysis of intracellular nucleotides. Rapid Communications in Mass Spectrometry 14 : 1625 (2000).*

Anderson et al., "Incorporation of pseudouridine into mRNA enhances translation by diminishing PKR activation," Nucleic Acids Res. 38(17):5884-92 (2010).
Chen et al., "LC/MS analysis of cellular RNA reveals NAD-linked RNA," Nat Chem Biol. 5(12):879-81 (2009).
Deltcheva et al., "CRISPR RNA maturation by trans-encoded small RNA and host factor RNase III," available in PMC Sep. 30, 2011, published in final edited form as: Nature 471(7340):602-7 (2011) (54 pages).
Derrigo et al., "RNA-protein interactions in the control of stability and localization of messenger RNA (review)," Int J Mol Med. 5(2):111-23 (2000).
Extended European Search Report for European Application No. 14770821.8, dated Oct. 21, 2016 (11 pages).
Farrow et al., "Combinatorial recombination of gene fragments to construct a library of chimeras," Curr Protoc Protein Sci. Chapter 26, Unit 26.2 (2010) (20 pages).
Gaj et al., "ZFN, TALEN, and CRISPR/Cas-based methods for genome engineering," Trends Biotechnol. 31(7):397-405 (2013).
Gilbert et al., "CRISPR-mediated modular RNA-guided regulation of transcription in eukaryotes," Cell 154(2):442-51 (2013) (15 pages).
Gonzalez et al., "Generation of mouse-induced pluripotent stem cells by transient expression of a single nonviral polycistronic vector," Proc. Natl. Acad. Sci. USA 106(22):8918-22 (2009).
Grosjean, Modification and editing of RNA: historical overview and important facts to remember. *Fine-Tuning of RNA Functions by Modification and Editing*. Grosjean H, 1-22 (2005).
Hamaguchi et al., "Direct reverse transcription-PCR on oligo(dT)-immobilized polypropylene microplates after capturing total mRNA from crude cell lysates," Clin Chem. 44(11):2256-63 (1998).
Hansen et al., "Circular RNA and miR-7 in Cancer," Cancer Res. 73(18):5609-12 (2013).
Hansen et al., "Natural RNA circles function as efficient microRNA sponges," Nature. 495(7441):384-8 (2013) (7 pages).
Hikishima et al., "Synthesis of 1,8-naphthyridine C-nucleosides and their base-pairing properties in oligodeoxynucleotides: thermally stable naphthyridine:imidazopyridopyrimidine base-pairing motifs," Angew Chem Int Ed. 44:596-8 (2005).
International Preliminary Report on Patentability and Written Opinion for International Patent Application No. PCT/US2014/026838, dated Sep. 15, 2015 (8 pages).
International Search Report for International Patent Application No. PCT/US2014/026838, dated Sep. 25, 2014 (4 pages).
Jakobsen et al., "Direct mRNA Isolation Using Magnetic Oligo (dT) Beads: A Protocol for All Types of Cell Cultures, Animal and Plant Tissues," Advances in Biomagnetic Separation. ed. Uhlén et al., Eaton Publishing, 61-71 (1994) (15 pages).
Jani et al., "In vitro transcription and capping of Gaussia luciferase mRNA followed by HeLa cell transfection," J Vis Exp. 61:e3702 (2012) (9 pages).
Kanwar et al., "Chimeric aptamers in cancer cell-targeted drug delivery," Crit Rev Biochem Mol Bio. 46(6):459-77 (2011).
Karikó et al., "Incorporation of pseudouridine into mRNA yields superior nonimmunogenic vector with increased translational capacity and biological stability." Mol Ther. 16(11):1833-40 (2008).
Karikó et al., "mRNA is an endogenous ligand for Toll-like receptor 3," J Biol Chem. 279(13): 12542-50 (2004).
Kluiver et al., "Rapid generation of MicroRNA Sponges for MicroRNA Inhibition ," PLoS One. 7(1):E29275(2012) (8 pages).
Kore et al., "Synthesis and application of 2'-fluoro-substituted cap analogs." Bioorg Med Chem Letters. 17:5295-9 (2007).
Kormann et al., "Expression of therapeutic proteins after delivery of chemically modified mRNA in mice," Nat Biotechnol. 29(2):154-7 (2011) (6 pages).
Kuwahara et al., "Molecular evolution of functional nucleic acids with chemical modifications," Molecules. 15(8):5423-44 (2010).
Kwoh et al., "Transcription-based amplification system and detection of amplified human immunodeficiency virus type 1 with a bead-based sandwich hybridization format," Proc Natl Acad Sci U S A. 86(4):1173-7 (1989).

* cited by examiner

(56) References Cited

OTHER PUBLICATIONS

Liu et al., "Construction of circular miRNA sponges targeting miR-21 or miR-221 and demonstration of their excellent anticancer effects on malignant melanoma cells," Int J Biochem Cell Biol. 45(11):2643-50 (2013).
Maeder et al., "Crispr RNA-guided activation of endogenous human genes," Nat Methods 10(10):977-9 (2013).
Memczak et al., "Circular RNAs are a large class of animal RNAs with regulatory potency," Nature. 495(7441):333-8 (2013) (10 pages).
Mestas et al., "Of mice and not men: differences between mouse and human immunology," J Immunol. 172(5):2731-8 (2004).
Mészáros et al., "Subtractive hybridization strategy using paramagnetic oligo(dT) beads and PCR," Biotechniques 20(3):413-9 (1996).
Okita et al., "Generation of mouse induced pluripotent stem cells without viral vectors," Science. 322(5903):949-53 (2008).
Park et al., "Reverse transcriptase-coupled quantitative real time PCR analysis of cell-free transcription on the chromatin-assembled p21 promoter," PLoS One 6(8):e23617 (2011) (6 pages).
Pascolo, Chapter 3: Vaccination With Messenger RNA. *Methods in Molecular Medicine*, vol. 127: *DNA Vaccines: Methods and Protocols*: Second Edition. Saltzman et al., Humana Press Inc., 23-40 (2006).
Perez-Pinera et al., "RNA-guided gene activation by CRISPR-Cas9-based transcription factors," Nat Methods 10(10):973-6 (2013).
PubChem Compound Summary for CID 262692, created Mar. 26, 2005. <URL: http://pubchem.ncbi.nlm.nih.gov/compound/262692> (11 pages).
PubChem Compound Summary for CID 479886, created Aug. 1, 2005. <URL: http://pubchem.ncbi.nlm.nih.gov/compound/479886> (12 pages).
Qiu et al., "Creating a flexible multiple microRNA expression vector by linking precursor microRNAs," Biochem Biophys Res Commun. 411(2):276-80 (2011).
Sasaki et al., "Construction of a normalized cDNA library by introduction of a semi-solid mRNA-cDNA hybridization system," Nucleic Acids Res. 22(6):987-92 (1994).
Shimelis et al., "Nuclease P1 digestion/high-performance liquid chromatography, a practical method for DNA quantitation," J Chromatogr A. 1117(2):132-6 (2006).
Slater, Chapter 16: The Purification of Poly(A)-Containing RNA by Affinity Chromatography. Methods in Molecular Biology. ed. Walker, Springer Verlag,117-20 (1985).
Smith et al., "Purification of polynucleotide phosphorylase by affinity chromatography and some properties of the purified enzymes," Nucleic Acids Res. 1(12):1763-73 (1974).
Stadtfeld et al., "Induced pluripotent stem cells generated without viral integration," Science. 322(5903):945-9 (2008).
Tavernier et al., "mRNA as gene therapeutic: how to control protein expression," J Control Release. 150(3):238-47 (2011).
Vomelová et al., "Methods of RNA purification. All ways (should) lead to Rome," Folia Biol (Praha) 55(6):243-51 (2009).
Wang et al., "One-step generation of mice carrying mutations in multiple genes by CRISPR/Cas-mediated genome engineering," Cell 153(4):910-8 (2013).
Warren et al., "Highly efficient reprogramming to pluripotency and directed differentiation of human cells with synthetic modified mRNA," Cell Stem Cell. 7(5):618-30 (2010).
Weiss et al., "Prophylactic mRNA vaccination against allergy," Curr Opin Allergy Clin Immunol. 10(6):567-74 (2010) (8 pages).
Wilusz et al., "Molecular Biology. A circuitous route to noncoding RNA," Science. 340(6131):440-1 (2013).
Yamamoto et al., "Current prospects for mRNA gene delivery," Eur J Pharm Biopharm. 71(3):484-9 (2009).
Yanagawa et al., "Overexpression of autocrine motility factor in metastatic tumor cells: possible association with augmented expression of KIF3A and GDI-beta," Lab Invest. 84(4):513-22 (2004).
Bellon et al., "Sugar modified oligonucleotides: synthesis, nuclease resistance and base pairing of oligodeoxynucleotides containing 1-(4'-thio-beta-D-ribofuranosyl)-thymine," Biochem Biophys Res Commun. 184(2):797-803 (1992).
Bellon et al., "4'-Thio-oligo-beta-D-ribonucleotides: synthesis of beta-4'-thio-oligouridylates, nuclease resistance, base pairing properties, and interaction with HIV-1 reverse transcriptase," Nucleic Acids Res. 21(7):1587-93 (1993).
Haeberli et al., "Syntheses of 4'-thioribonucleosides and thermodynamic stability and crystal structure of RNA oligomers with incorporated 4'-thiocytosine," Nucleic Acids Res. 33(13):3965-75 (2005).
"Potato spindle tuber viroid," Wikipedia, <https://en.wikipedia.org/wiki/Potato_spindle_tuber_viroid>, accessed Jan. 19, 2017 (2 pages).
Colpan et al., "Large-scale purification of viroid RNA using Cs2SO4 gradient centrifugation and high-performance liquid chromatography," Anal Biochem. 131(1):257-65 (1983).
Kazantsev et al., "Crystal structure of a bacterial ribonuclease P RNA," Proc Natl Acad Sci U.S.A. 102(38):13392-7 (2005).
Weill et al., "Translational control by changes in poly(A) tail length: recycling mRNAs," Nat Struct Mol Biol. 19(6):577-85 (2012).
Jeck et al., "Circular RNAs are abundant, conserved, and associated with ALU repeats," RNA 19(2):141-57 (2013) (19 pages).
Minuth et al., "A nucleobase analogue that pairs strongly with adenine," Angew Chem Int Ed Engl. 52(41):10874-7 (2013).
Gjerde et al. RNA Purification and Analysis: Sample Preparation, Extraction, Chromatography, <http://onlinelibrary.wiley.com/book/10.1002/9783527627196> retrieved on Jul. 18, 2014 (203 pages).
Lapham et al. "RNase H cleavage for processing of in vitro transcribed RNA for NMR studies and RNA ligation." RNA. 2(3)289-96 (1996).
Wang et al. "Characterization of mutation spectra with ultra-deep pyrosequencing: application to HIV-1 drug resistance." Genome Res. 17(8):1195-201 (2007).
Carmody et al. "Purity and Content Analysis of Oligonucleotidesby Capillary Gel Electrophoresis" <http://www.nbchem.de/mediapool/120/1202675/data/K11050_C007.pdf> retrieved on Jul. 18, 2014 (22 pages).
Xu et al. "Tutorial: Capillary Electrophoresis" <http://web.colby.edu/ch332public/files/2012/02/CE_tutorial.pdf> retrieved on Jul. 18, 2014 (14 pages).
Azarani, et al. "RNA analysis by ion-pair reversed-phase high performance liquid chromatography." Nucleic Acids Res. 29(2):E7 (2001).
McCarthy et al. "Reversed-phase ion-pair liquid chromatography analysis and purification of small interfering RNA" Anal Biochem. 390(2):181-8 (2009).
Chien et al. "RNA:DNA hybrids are more stable than DNA:DNA duplexes in concentrated perchlorate and trichloroacetate solutions." Nucleic Acids Res. 5(5):1627-37 (1978).
Gjerde et al. "RNA Purification and Analysis: Sample Preparation, Extraction, Chromatography," <http://onlinelibrary.wiley.com/book/10.1002/9783527627196> retrieved on Jul. 18, 2014 (203 pages).
Azarani, et al. "RNA analysis by ion-pair reversed-phase high performance liquid chromatography." Nucleic Acids Res. 29(2):E7 (2001) (9 pages).
Dickman "Ion Pair Reverse-Phase Chromatography: A Versatile Platform for the Analysis of RNA" «http://www.chromatographytoday.com/articles/prep-chiral-green-incsfc-gpc-ion/33/m._j._dickman/ion_pair_reverse-phase_chromatography_a_versatile_platform_for_the_analysis_of_rna/984/> retrieved on Oct. 16, 2015 (5 pages).
Kim et al. "Rapid purification of RNAs using fast performance liquid chromatography (FPLC)." RNA. 13(2):289-94 (2007).
McKenna et al. "Purification and characterization of transcribed RNAs using gel filtration chromatography." Nat Protoc. 2(12):3270-7 (2007).
Reyes-Engel and Dieguez-Lucena, "Direct quantification of specific mRNA using a selected biotinylated oligonucleotide by free solution capillary electrophoresis," Nucleic Acids Res, 21 (3):759-760, 1993.
Irier et al., "Translational regulation of GluR2 mRNAs in rat hippocampus by alternative 3' untranslated regions," J. Neurochem, 109(2):584-594, 2009 (18 pages).

(56) References Cited

OTHER PUBLICATIONS

Mitra, "Using analytical ultracentrifugation (AUC) to measure global conformational changes accompanying equilibrium tertiary folding of RNA molecules," Methods in Enzymology, 2009(469):209-36 (2009).
Third-Party Submission under 37 CFR 1.290 for U.S. Appl. No. 14/776,893, submitted Aug. 31, 2016 (3 pages).
Cross et al., "Analysis of small nuclear ribonucleoproteins (RNPs) in Trypanosoma brucei: structural organization and protein components of the spliced leader RNP," Mol Cell Biol. 11(11):5516-5526 (1991).
Farrell, "Related Techniques," RNA Methodologies. 475 (2005) (6 pages).
Theus et al., "A simple assay for determining the capping efficiencies of RNA polymerases used for in vitro transcription," Biotechniques. 9(5):610-2, 614-5 (1990).
Vera et al., "Combination of in vitro capping and ribonuclease protection improves the detection of transcription start sites in chloroplasts," Plant Mol Biol. 19(2):309-11 (1992).
Crain, "Preparation and enzymatic hydrolysis of DNA and RNA for mass spectrometry," Methods in Enzymology, 193:782-790, 1990.†
Pomerantz and McCloskey, "Analysis of RNA Hydrolyzates by liquid chromatography-mass spectrometry," Methods in Enzymology, 193:796-824, 1990.†
Liu et al., "In vitro Transcription on DNA Templates Immobilized to Streptavidin MagneSphere(r) Paramagnetic Particles," Promega Notes, No. 64, p. 21, 1997.†

\* cited by examiner
† cited by third party

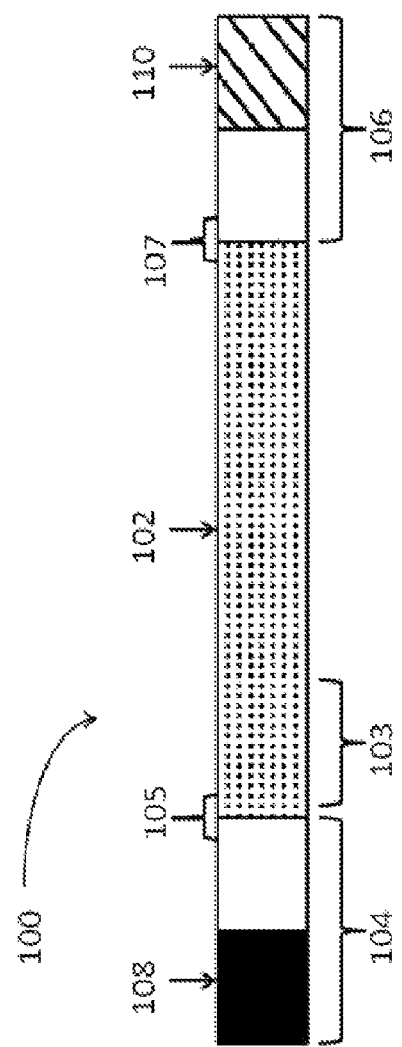

REMOVAL OF DNA FRAGMENTS IN MRNA PRODUCTION PROCESS

BACKGROUND OF THE INVENTION

Field of the Invention

The invention relates to methods for the removal of DNA from a sample during the mRNA production process.

Description of the Related Art

RNA polymerase does not synthesize mRNA de novo, therefore a DNA template that contains a T7 promoter sequence upstream of the protein coding sequence and a poly A tail downstream of the coding sequence is necessary for an in vitro transcription (IVT) reaction to be performed. Following the enzymatic synthesis of mRNA, it is important to remove the DNA template.

The DNA template used in the mRNA manufacturing process must be removed to ensure the efficacy of therapeutics and safety, because residual DNA in drug products may induce activation of the innate response and has the potential to be oncogenic in patient populations. Regulatory guidelines may also require the quantification, control, and removal of the DNA template in RNA products. Currently available or reported methods do not address this deficiency.

REFERENCE TO A SEQUENCE LISTING

This application contains a Sequence Listing in computer readable form. The computer readable form is incorporated herein by reference.

SUMMARY OF THE INVENTION

The present invention provides methods for removing a DNA template from a sample comprising said DNA template and an RNA transcript. In one embodiment, the method involves obtaining the sample and subjecting it to a procedure that removes the DNA from the sample and produces a product comprising the RNA transcript. For example, the method may be DNase treatment, or the removal of labeled DNA. In another embodiment, the RNA transcript is the product of in vitro transcription using a non-amplified DNA template. In a separate embodiment, the RNA transcript is a full length RNA transcript. For example, the RNA transcript can be between 400 and 10,000 nucleotides in length, or between 700 and 3,000 nucleotides in length. In a further embodiment, the RNA transcript comprises chemically modified mRNA nucleotides.

DNase treatment is one method of removing a DNA template from a sample, in an embodiment. For example, DNase I can be added to the sample. In some embodiments, 10 units, 2 units, 1 unit, 0.5 units, or 0.05 units of DNase I are added for each μg of DNA template in the sample. In an embodiment, the DNase I is incubated with the sample at 37° Celsius for one hour. In another embodiment, the digested DNA template is separated from the RNA transcript after DNase treatment. In a further embodiment, the separating step may involve centrifugation, ultrafiltration, precipitation, liquid chromatography, gel electrophoresis, or use of a vacuum column.

In another embodiment, after an in vitro transcription reaction product is treated with DNase, a portion of the product is contacted with a nuclease (for example, nuclease P1) under conditions that promote nucleotide digestion to obtain a digested product. Next, the digested product is analyzed by liquid chromatography-tandem mass spectrometry, and the presence or absence of residual deoxynucleotides is detected in the digested product based on the liquid chromatography-tandem mass spectrometry analysis. In some examples, the total abundance of deoxynucleotides in the mass spectrometry analysis is either <500 ppm, <300 ppm, <250 ppm, <100 ppm, <50 ppm, <25 ppm, <10 ppm, <5 ppm, <1 ppm, or <0.2 ppm.

In an embodiment, the DNase is attached to a solid support, for example a solid phase resin, controlled pore glass, polystyrene, polystyrene divinyl benzene, cellulose, polyacrylamide, silica, polymethacrylate, or a dextran based polymer.

Removing labeled DNA is another method of removing a DNA template from a sample. In one embodiment, the DNA template includes a label, and the DNA removal procedure includes removal of labeled DNA from a sample by contacting the sample with a solid support configured to bind the label. The solid support could be, for example, a streptavidin resin, a N-hydroxysuccinimide-activated resin, an epoxide resin, an aldehyde resin, cyanine 3-NHS ester, or cyanine 5-NHS ester. In some embodiments, the DNA template is a plasmid. In further embodiments, the plasmid may be coupled to the label either before or after the plasmid has been linearized by a restriction enzyme. In other embodiments, the DNA template is a PCR product. In one example, the DNA template is produced by amplifying a DNA molecule where a primer used in the amplifying is coupled to the label. In a further example, the primer is chemically synthesized. In a further example, the label is coupled to the 5'-end of the DNA template. In some embodiments, the label is a reactive group, such as a biotin, an amine, or a thiol. In further embodiments, the biotin is coupled to the DNA template by an alkylation reaction.

In another embodiment, the DNA template is produced by amplifying a DNA molecule where the label is coupled to the DNA molecule by a DNA polymerase. In one embodiment, the label comprises modified nucleotides, such as 5-aminoallyl pyrimidine NTPS or N-6-aminohexyl cytidine NTPs. In a further embodiment, the modified nucleotides comprise nucleotide analogs coupled to an intrinsic linker.

BRIEF DESCRIPTION OF THE SEVERAL VIEWS OF THE DRAWINGS

These and other features, aspects, and advantages of the present invention will become better understood with regard to the following description, and accompanying drawing, where:

FIG. 1 illustrates a schematic of a primary nucleotide construct, in accordance with an embodiment of the invention.

DETAILED DESCRIPTION OF THE INVENTION

Briefly, and as described in more detail below, described herein are methods for characterizing large mRNA transcripts using procedures such as oligonucleotide mapping, reverse transcriptase sequencing, charge distribution analysis, and detection of RNA impurities. Analyses of these procedures are performed using a variety of techniques, including high performance liquid chromatography (HPLC), anion exchange HPLC, capillary electrophoresis (CE), Sanger sequencing, ion pair reverse phase HPLC, and electrospray ionization.

Definitions

Terms used in the claims and specification are defined as set forth below unless otherwise specified.

At various places in the present specification, substituents of compounds of the present disclosure are disclosed in groups or in ranges. It is specifically intended that the present disclosure include each and every individual subcombination of the members of such groups and ranges. For example, the term "C1-6 alkyl" is specifically intended to individually disclose methyl, ethyl, C3 alkyl, C4 alkyl, C5 alkyl, and C6 alkyl.

About: As used herein, the term "about" means +/−10% of the recited value.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," "coupled," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It may also suggest ionic or hydrogen bonding or a hybridization based connectivity sufficiently stable such that the "associated" entities remain physically associated.

Amino: the term "amino," as used herein, represents —N($R^{N1}$)$_2$, wherein each $R^{N1}$ is, independently, H, OH, NO$_2$, N($R^{N2}$)$_2$, SO$_2$OR$^{N2}$, SO$_2$R$^{N2}$, SOR$^{N2}$, an N-protecting group, alkyl, alkenyl, alkynyl, alkoxy, aryl, alkaryl, cycloalkyl, alkcycloalkyl, carboxyalkyl, sulfoalkyl, heterocyclyl (e.g., heteroaryl), or alkheterocyclyl (e.g., alkheteroaryl), wherein each of these recited $R^{N1}$ groups can be optionally substituted, as defined herein for each group; or two $R^{N1}$ combine to form a heterocyclyl or an N-protecting group, and wherein each $R^{N2}$ is, independently, H, alkyl, or aryl. The amino groups of the invention can be an unsubstituted amino (i.e., —NH$_2$) or a substituted amino (i.e., —N($R^{N1}$)$_2$). In a preferred embodiment, amino is —NH$_2$ or —NHR$^{N1}$, wherein $R^{N1}$ is, independently, OH, NO$_2$, NH$_2$, NR$^{N2}$$_2$, SO$_2$OR$^{N2}$, SO$_2$R$^{N2}$, SOR$^{N2}$, alkyl, carboxyalkyl, sulfoalkyl, or aryl, and each $R^{N2}$ can be H, C$_{1-20}$ alkyl (e.g., C$_{1-6}$ alkyl), or C$_{6-10}$ aryl.

Label: As used herein, "label" refers to one or more markers, signals, or moieties which are attached, incorporated or associated with another entity that is readily detected by methods known in the art including radiography, fluorescence, chemiluminescence, enzymatic activity, absorbance and the like. Detectable labels include radioisotopes, fluorophores, chromophores, enzymes, dyes, metal ions, ligands such as biotin, avidin, streptavidin and haptens, quantum dots, and the like. Detectable labels may be located at any position in the peptides or proteins disclosed herein. They may be within the amino acids, the peptides, or proteins, or located at the N- or C-termini.

DNA template: As used herein, a DNA template refers to a polynucleotide template for RNA polymerase. Typically a DNA template includes the sequence for a gene of interest operably linked to a RNA polymerase promoter sequence.

Digest: As used herein, the term "digest" means to break apart into smaller pieces or components. When referring to polypeptides or proteins, digestion results in the production of peptides. When referring to mRNA, digestion results in the production of oligonucleotide fragments.

Engineered: As used herein, embodiments of the invention are "engineered" when they are designed to have a feature or property, whether structural or chemical, that varies from a starting point, wild type or native molecule.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Fragment: A "fragment," as used herein, refers to a portion. For example, fragments of proteins may comprise polypeptides obtained by digesting full-length protein isolated from cultured cells.

Gene of interest: As used herein, "gene of interest" refers to a polynucleotide which encodes a polypeptide or protein of interest. Depending on the context, the gene of interest refers to a deoxyribonucleic acid, e.g., a gene of interest in a DNA template which can be transcribed to an RNA transcript, or a ribonucleic acid, e.g., a gene of interest in an RNA transcript which can be translated to produce the encoded polypeptide of interest in vitro, in vivo, in situ or ex vivo. As described in more detail below, a polypeptide of interest includes but is not limited to, biologics, antibodies, vaccines, therapeutic proteins or peptides, etc.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe or cell or tissue thereof).

Isolated: As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" it is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof. Methods for isolating compounds and their salts are routine in the art.

Modified: As used herein "modified" refers to a changed state or structure of a molecule of the invention. Molecules may be modified in many ways including chemically, structurally, and functionally. In one embodiment, the mRNA molecules of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like. For example, a gene of interest operably linked to an RNA polymerase promoter allows transcription of the gene of interest.

Peptide: As used herein, "peptide" is less than or equal to 50 amino acids long, e.g., about 5, 10, 15, 20, 25, 30, 35, 40, 45, or 50 amino acids long.

Poly A tail: As used herein, "poly A tail" refers to a chain of adenine nucleotides. The term can refer to poly A tail that is to be added to an RNA transcript, or can refer to the poly A tail that already exists at the 3' end of an RNA transcript. As described in more detail below, a poly A tail is typically 5-300 nucleotides in length.

Purified: As used herein, "purify," "purified," "purification" means to make substantially pure or clear from unwanted components, material defilement, admixture or imperfection.

RNA transcript: As used herein, an "RNA transcript" refers to a ribonucleic acid produced by an in vitro transcription reaction using a DNA template and an RNA polymerase. As described in more detail below, an RNA transcript typically includes the coding sequence for a gene of interest and a poly A tail. RNA transcript includes an mRNA. The RNA transcript can include modifications, e.g., modified nucleotides. As used herein, the term RNA transcript includes and is interchangeable with mRNA, modified mRNA "mmRNA" or modified mRNA, and primary construct.

Signal Sequences: As used herein, the phrase "signal sequences" refers to a sequence which can direct the transport or localization of a protein.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Stable: As used herein "stable" refers to a compound that is sufficiently robust to survive isolation to a useful degree of purity from a reaction mixture, and preferably capable of formulation into an efficacious therapeutic agent.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals such as mice, rats, rabbits, non-human primates, and humans) and/or plants.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Synthetic: The term "synthetic" means produced, prepared, and/or manufactured by the hand of man. Synthesis of polynucleotides or polypeptides or other molecules of the present invention may be chemical or enzymatic.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules.

Unmodified: As used herein, "unmodified" refers to any substance, compound or molecule prior to being changed in any way. Unmodified may, but does not always, refer to the wild type or native form of a biomolecule. Molecules may undergo a series of modifications whereby each modified molecule may serve as the "unmodified" starting molecule for a subsequent modification.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Compositions of the Invention

The present invention provides nucleic acid molecules, specifically polynucleotides, primary constructs and/or mRNA which encode one or more polypeptides of interest. The term "nucleic acid," in its broadest sense, includes any compound and/or substance that comprise a polymer of nucleotides. These polymers are often referred to as polynucleotides. Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

In preferred embodiments, the nucleic acid molecule is a messenger RNA (mRNA). As used herein, the term "messenger RNA" (mRNA) refers to any polynucleotide which encodes a polypeptide of interest and which is capable of being translated to produce the encoded polypeptide of interest in vitro, in vivo, in situ or ex vivo.

Traditionally, the basic components of an mRNA molecule include at least a coding region, a 5'UTR, a 3'UTR, a 5' cap and a poly-A tail. Building on this wild type modular structure, the present invention expands the scope of functionality of traditional mRNA molecules by providing polynucleotides or primary RNA constructs which maintain a modular organization, but which comprise one or more structural and/or chemical modifications or alterations which impart useful properties to the polynucleotide including, in some embodiments, the lack of a substantial induction of the innate immune response of a cell into which the polynucleotide is introduced. As such, modified mRNA molecules of the present invention are termed "mmRNA." As used herein, a "structural" feature or modification is one in which two or more linked nucleotides are inserted, deleted, duplicated, inverted or randomized in a polynucleotide, primary construct or mmRNA without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" may be chemically modified to "AT-5meC-G". The same polynucleotide may be structurally modified from "ATCG" to "ATCCCG". Here, the dinucleotide "CC" has been inserted, resulting in a structural modification to the polynucleotide.

mRNA Architecture

FIG. 1 shows a representative polynucleotide primary construct 100 of the present invention. As used herein, the term "primary construct" or "primary mRNA construct" refers to a polynucleotide transcript which encodes one or more polypeptides of interest and which retains sufficient structural and/or chemical features to allow the polypeptide of interest encoded therein to be translated. Primary constructs may be polynucleotides of the invention. When structurally or chemically modified, the primary construct may be referred to as an mmRNA ("modified mRNA"). Modified RNA, e.g., RNA transcripts, e.g., mRNA, are disclosed in the following which is incorporated by reference for all purposes: U.S. patent application Ser. No. 13/791,922, "Modified Polynucleotides for the Production of Biologics and Proteins Associated with Human Disease", filed Mar. 9, 2013.

Returning to FIG. 1, the primary construct 100 here contains a first region of linked nucleotides 102 that is flanked by a first flanking region 104 and a second flaking region 106. As used herein, the "first region" may be referred to as a "coding region" or "region encoding" or simply the "first region." This first region may include, but is not limited to, the encoded polypeptide of interest. The polypeptide of interest may comprise at its 5' terminus one or more signal sequences encoded by a signal sequence region 103. The flanking region 104 may comprise a region of linked nucleotides comprising one or more complete or incomplete 5' UTRs sequences. The flanking region 104 may also comprise a 5' terminal cap 108. The second flanking region 106 may comprise a region of linked nucleotides comprising one or more complete or incomplete 3' UTRs. The flanking region 106 may also comprise a 3' tailing sequence 110.

Bridging the 5' terminus of the first region 102 and the first flanking region 104 is a first operational region 105. Traditionally this operational region comprises a Start codon. The operational region may alternatively comprise any translation initiation sequence or signal including a Start codon.

Bridging the 3' terminus of the first region 102 and the second flanking region 106 is a second operational region 107. Traditionally this operational region comprises a Stop codon. The operational region may alternatively comprise any translation initiation sequence or signal including a Stop codon. According to the present invention, multiple serial stop codons may also be used.

Generally, the shortest length of the first region of the primary construct of the present invention can be the length of a nucleic acid sequence that is sufficient to encode for a dipeptide, a tripeptide, a tetrapeptide, a pentapeptide, a hexapeptide, a heptapeptide, an octapeptide, a nonapeptide, or a decapeptide. In another embodiment, the length may be sufficient to encode a peptide of 2-30 amino acids, e.g. 5-30, 10-30, 2-25, 5-25, 10-25, or 10-20 amino acids. The length may be sufficient to encode for a peptide of at least 11, 12, 13, 14, 15, 17, 20, 25 or 30 amino acids, or a peptide that is no longer than 40 amino acids, e.g. no longer than 35, 30, 25, 20, 17, 15, 14, 13, 12, 11 or 10 amino acids. Examples of dipeptides that the polynucleotide sequences can encode or include, but are not limited to, carnosine and anserine.

Generally, the length of the first region encoding the polypeptide of interest of the present invention is greater than about 30 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides). As used herein, the "first region" may be referred to as a "coding region" or "region encoding" or simply the "first region."

In some embodiments, the polynucleotide, primary construct, or mmRNA includes from about 30 to about 100,000 nucleotides (e.g., from 100-10,000, from 600-10,000, from 700-3,000, from 30 to 50, from 30 to 100, from 30 to 250, from 30 to 500, from 30 to 1,000, from 30 to 1,500, from 30 to 3,000, from 30 to 5,000, from 30 to 7,000, from 30 to 10,000, from 30 to 25,000, from 30 to 50,000, from 30 to 70,000, from 100 to 250, from 100 to 500, from 100 to 1,000, from 100 to 1,500, from 100 to 3,000, from 100 to 5,000, from 100 to 7,000, from 100 to 10,000, from 100 to 25,000, from 100 to 50,000, from 100 to 70,000, from 100 to 100,000, from 500 to 1,000, from 500 to 1,500, from 500 to 2,000, from 500 to 3,000, from 500 to 5,000, from 500 to 7,000, from 500 to 10,000, from 500 to 25,000, from 500 to 50,000, from 500 to 70,000, from 500 to 100,000, from 1,000 to 1,500, from 1,000 to 2,000, from 1,000 to 3,000, from 1,000 to 5,000, from 1,000 to 7,000, from 1,000 to 10,000, from 1,000 to 25,000, from 1,000 to 50,000, from 1,000 to 70,000, from 1,000 to 100,000, from 1,500 to 3,000, from 1,500 to 5,000, from 1,500 to 7,000, from 1,500 to 10,000, from 1,500 to 25,000, from 1,500 to 50,000, from 1,500 to 70,000, from 1,500 to 100,000, from 2,000 to 3,000, from 2,000 to 5,000, from 2,000 to 7,000, from 2,000 to 10,000, from 2,000 to 25,000, from 2,000 to 50,000, from 2,000 to 70,000, and from 2,000 to 100,000).

According to the present invention, the first and second flanking regions may range independently from 15-1,000 nucleotides in length (e.g., greater than 30, 40, 45, 50, 55, 60, 70, 80, 90, 100, 120, 140, 160, 180, 200, 250, 300, 350, 400, 450, 500, 600, 700, 800, and 900 nucleotides or at least 30, 40, 45, 50, 55, 60, 70, 80, 90, 100, 120, 140, 160, 180, 200, 250, 300, 350, 400, 450, 500, 600, 700, 800, 900, and 1,000 nucleotides).

According to the present invention, the tailing sequence may range from absent to 500 nucleotides in length (e.g., at least 60, 70, 80, 90, 120, 140, 160, 180, 200, 250, 300, 350, 400, 450, or 500 nucleotides). Where the tailing region is a polyA tail, the length may be determined in units of or as a function of polyA Binding Protein binding. In this embodiment, the polyA tail is long enough to bind at least 4 monomers of PolyA Binding Protein. PolyA Binding Protein monomers bind to stretches of approximately 38 nucleotides. As such, it has been observed that polyA tails of about 80 nucleotides and 160 nucleotides are functional.

According to the present invention, the capping region may comprise a single cap or a series of nucleotides forming the cap. In this embodiment the capping region may be from 1 to 10, e.g. 2-9, 3-8, 4-7, 1-5, 5-10, or at least 2, or 10 or fewer nucleotides in length. In some embodiments, the cap is absent.

According to the present invention, the first and second operational regions may range from 3 to 40, e.g., 5-30, 10-20, 15, or at least 4, or 30 or fewer nucleotides in length and may comprise, in addition to a Start and/or Stop codon, one or more signal and/or restriction sequences.

Flanking Regions: Untranslated Regions (UTRs)

Untranslated regions (UTRs) of a gene are transcribed but not translated. The 5'UTR starts at the transcription start site and continues to the start codon but does not include the start codon; whereas, the 3'UTR starts immediately following the stop codon and continues until the transcriptional termination signal. There is growing body of evidence about the regulatory roles played by the UTRs in terms of stability of the nucleic acid molecule and translation. The regulatory features of a UTR can be incorporated into the polynucleotides, primary constructs and/or mmRNA ("modified mRNA") of the present invention to enhance the stability of the molecule. The specific features can also be incorporated to ensure controlled down-regulation of the transcript in case they are misdirected to undesired sites.

5' UTR and Translation Initiation

Natural 5'UTRs bear features which play roles in for translation initiation. They harbor signatures like Kozak sequences which are commonly known to be involved in the process by which the ribosome initiates translation of many genes. Kozak sequences have the consensus CCR(A/G)CCAUGG, where R is a purine (adenine or guanine) three bases upstream of the start codon (AUG), which is followed by another 'G'. 5'UTR also have been known to form secondary structures which are involved in elongation factor binding.

By engineering the features typically found in abundantly expressed genes of specific target organs, one can enhance the stability and protein production of the polynucleotides, primary constructs or mmRNA of the invention. For example, introduction of 5' UTR of liver-expressed mRNA, such as albumin, serum amyloid A, Apolipoprotein A/B/E, transferrin, alpha fetoprotein, erythropoietin, or Factor VIII, could be used to enhance expression of a nucleic acid molecule, such as a mmRNA, in hepatic cell lines or liver. Likewise, use of 5' UTR from other tissue-specific mRNA to improve expression in that tissue is possible for muscle (MyoD, Myosin, Myoglobin, Myogenin, Herculin), for endothelial cells (Tie-1, CD36), for myeloid cells (C/EBP, AML1, G-CSF, GM-CSF, CD11b, MSR, Fr-1, i-NOS), for leukocytes (CD45, CD18), for adipose tissue (CD36, GLUT4, ACRP30, adiponectin) and for lung epithelial cells (SP-A/B/C/D).

Other non-UTR sequences may be incorporated into the 5' (or 3' UTR) UTRs. For example, introns or portions of introns sequences may be incorporated into the flanking regions of the polynucleotides, primary constructs or mmRNA of the invention. Incorporation of intronic sequences may increase protein production as well as mRNA levels.

3' UTR and the AU Rich Elements

3' UTRs are known to have stretches of Adenosines and Uridines embedded in them. These AU rich signatures are particularly prevalent in genes with high rates of turnover. Based on their sequence features and functional properties, the AU rich elements (AREs) can be separated into three classes (Chen et al, 1995): Class I AREs contain several dispersed copies of an AUUUA motif within U-rich regions. C-Myc and MyoD contain class I AREs. Class II AREs possess two or more overlapping UUAUUUA(U/A)(U/A) nonamers. Molecules containing this type of AREs include GM-CSF and TNF-a. Class III ARES are less well defined. These U rich regions do not contain an AUUUA motif c-Jun and Myogenin are two well-studied examples of this class. Most proteins binding to the AREs are known to destabilize the messenger, whereas members of the ELAV family, most notably HuR, have been documented to increase the stability of mRNA. HuR binds to AREs of all the three classes. Engineering the HuR specific binding sites into the 3' UTR of nucleic acid molecules will lead to HuR binding and thus, stabilization of the message in vivo.

Introduction, removal or modification of 3' UTR AU rich elements (AREs) can be used to modulate the stability of polynucleotides, primary constructs or mmRNA of the invention. When engineering specific polynucleotides, primary constructs or mmRNA, one or more copies of an ARE can be introduced to make polynucleotides, primary constructs or mmRNA of the invention less stable and thereby curtail translation and decrease production of the resultant protein. Likewise, AREs can be identified and removed or mutated to increase the intracellular stability and thus increase translation and production of the resultant protein. Transfection experiments can be conducted in relevant cell lines, using polynucleotides, primary constructs or mmRNA of the invention and protein production can be assayed at various time points post-transfection. For example, cells can be transfected with different ARE-engineering molecules and by using an ELISA kit to the relevant protein and assaying protein produced at 6 hour, 12 hour, 24 hour, 48 hour, and 7 days post-transfection.

5' Capping

The 5' cap structure of an mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns removal during mRNA splicing.

Endogenous mRNA molecules may be 5'-end capped generating a 5'-ppp-5'-triphosphate linkage between a terminal guanosine cap residue and the 5'-terminal transcribed sense nucleotide of the mRNA molecule. This 5'-guanylate cap may then be methylated to generate an N7-methyl-guanylate residue. The ribose sugars of the terminal and/or anteterminal transcribed nucleotides of the 5' end of the mRNA may optionally also be 2'-O-methylated. 5'-decapping through hydrolysis and cleavage of the guanylate cap structure may target a nucleic acid molecule, such as an mRNA molecule, for degradation.

Modifications to the polynucleotides, primary constructs, and mmRNA of the present invention may generate a non-hydrolyzable cap structure preventing decapping and thus increasing mRNA half-life. Because cap structure hydrolysis requires cleavage of 5'-ppp-5' phosphorodiester linkages, modified nucleotides may be used during the capping reaction. For example, a Vaccinia Capping Enzyme from New England Biolabs (Ipswich, Mass.) may be used with α-thio-guanosine nucleotides according to the manufacturer's instructions to create a phosphorothioate linkage in the 5'-ppp-5' cap. Additional modified guanosine nucleotides may be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the mRNA (as mentioned above) on the 2'-hydroxyl group of the sugar ring. Multiple distinct 5'-cap structures can be used to generate the 5'-cap of a nucleic acid molecule, such as an mRNA molecule.

Cap analogs, which herein are also referred to as synthetic cap analogs, chemical caps, chemical cap analogs, or structural or functional cap analogs, differ from natural (i.e. endogenous, wild-type or physiological) 5'-caps in their chemical structure, while retaining cap function. Cap analogs may be chemically (i.e. non-enzymatically) or enzymatically synthesized and/or linked to a nucleic acid molecule.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine ($m^7$G-3'mppp-G; which may equivalently be designated 3' O-Me-m7G(5')ppp(5')G). The 3'-O atom of the other, unmodified, guanine becomes linked to the 5'-terminal nucleotide of the capped nucleic acid molecule (e.g. an mRNA or mmRNA). The N7- and 3'-O-methlyated guanine provides the terminal moiety of the capped nucleic acid molecule (e.g. mRNA or mmRNA).

Another exemplary cap is mCAP, which is similar to ARCA but has a 2'-O-methyl group on guanosine (i.e., N7,2'-O-dimethyl-guanosine-5'-triphosphate-5'-guanosine, $m^7$Gm-ppp-G).

While cap analogs allow for the concomitant capping of a nucleic acid molecule in an in vitro transcription reaction, up to 20% of transcripts can remain uncapped. This, as well as the structural differences of a cap analog from an endogenous 5'-cap structures of nucleic acids produced by the endogenous, cellular transcription machinery, may lead to reduced translational competency and reduced cellular stability.

Polynucleotides, primary constructs and mmRNA of the invention may also be capped post-transcriptionally, using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present invention are those which, among other things, have enhanced binding of cap binding proteins, increased half life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of an mRNA and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N,pN2p (cap 0), 7mG(5')ppp(5')NlmpNp (cap 1), and 7mG(5')-ppp(5')NlmpN2mp (cap 2).

Because the polynucleotides, primary constructs or mmRNA may be capped post-transcriptionally, and because this process is more efficient, nearly 100% of the polynucleotides, primary constructs or mmRNA may be capped. This is in contrast to ~80% when a cap analog is linked to an mRNA in the course of an in vitro transcription reaction.

According to the present invention, 5' terminal caps may include endogenous caps or cap analogs. According to the present invention, a 5' terminal cap may comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

Poly-A Tails

During RNA processing, a long chain of adenine nucleotides (poly-A tail) may be added to a polynucleotide such as an mRNA molecules in order to increase stability. Immediately after transcription, the 3' end of the transcript may be cleaved to free a 3' hydroxyl. Then poly-A polymerase adds a chain of adenine nucleotides to the RNA. The process, called polyadenylation, adds a poly-A tail that can be between, for example, approximately 100 and 250 residues long.

It has been discovered that unique poly-A tail lengths provide certain advantages to the polynucleotides, primary constructs or mmRNA of the present invention.

Generally, the length of a poly-A tail of the present invention is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides). In some embodiments, the polynucleotide, primary construct, or mmRNA includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In one embodiment, the poly-A tail is designed relative to the length of the overall polynucleotides, primary constructs or mmRNA. This design may be based on the length of the coding region, the length of a particular feature or region (such as the first or flanking regions), or based on the length of the ultimate product expressed from the polynucleotides, primary constructs or mmRNA.

In this context the poly-A tail may be 10, 20, 30, 40, 50, 60, 70, 80, 90, or 100% greater in length than the polynucleotides, primary constructs or mmRNA or feature thereof. The poly-A tail may also be designed as a fraction of polynucleotides, primary constructs or mmRNA to which it belongs. In this context, the poly-A tail may be 10, 20, 30, 40, 50, 60, 70, 80, or 90% or more of the total length of the construct or the total length of the construct minus the poly-A tail. Further, engineered binding sites and conjugation of polynucleotides, primary constructs or mmRNA for Poly-A binding protein may enhance expression.

Additionally, multiple distinct polynucleotides, primary constructs or mmRNA may be linked together to the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In one embodiment, the polynucleotide primary constructs of the present invention are designed to include a polyA-G Quartet. The G-quartet is a cyclic hydrogen bonded array of four guanine nucleotides that can be formed by G-rich sequences in both DNA and RNA. In this embodiment, the G-quartet is incorporated at the end of the poly-A tail. The resultant mmRNA construct is assayed for stability, protein production and other parameters including half-life at various time points. It has been discovered that the polyA-G quartet results in protein production equivalent to at least 75% of that seen using a poly-A tail of 120 nucleotides alone.

Modifications

Herein, in a polynucleotide (such as a primary construct or an mRNA molecule), the terms "modification" or, as appropriate, "modified" refer to modification with respect to A, G, U or C ribonucleotides. Generally, herein, these terms are not intended to refer to the ribonucleotide modifications in naturally occurring 5'-terminal mRNA cap moieties. In a polypeptide, the term "modification" refers to a modification as compared to the canonical set of 20 amino acids, moiety.

The modifications may be various distinct modifications. In some embodiments, the coding region, the flanking regions and/or the terminal regions may contain one, two, or more (optionally different) nucleoside or nucleotide modifications. In some embodiments, a modified polynucleotide, primary construct, or mmRNA introduced to a cell may exhibit reduced degradation in the cell, as compared to an unmodified polynucleotide, primary construct, or mmRNA.

The polynucleotides, primary constructs, and mmRNA can include any useful modification, such as to the sugar, the nucleobase, or the internucleoside linkage (e.g. to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications according to the present invention may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

As described herein, the polynucleotides, primary constructs, and mmRNA of the invention do not substantially induce an innate immune response of a cell into which the mRNA is introduced. Features of an induced innate immune response include 1) increased expression of pro-inflammatory cytokines, 2) activation of intracellular PRRs (RIG-I, MDA5, etc, and/or 3) termination or reduction in protein translation.

In certain embodiments, it may desirable to intracellularly degrade a modified nucleic acid molecule introduced into the cell. For example, degradation of a modified nucleic acid molecule may be preferable if precise timing of protein production is desired. Thus, in some embodiments, the invention provides a modified nucleic acid molecule containing a degradation domain, which is capable of being acted on in a directed manner within a cell. In another aspect, the present disclosure provides polynucleotides comprising a nucleoside or nucleotide that can disrupt the binding of a major groove interacting, e.g. binding, partner with the polynucleotide (e.g., where the modified nucleotide has decreased binding affinity to major groove interacting partner, as compared to an unmodified nucleotide).

The polynucleotides, primary constructs, and mmRNA can optionally include other agents (e.g., RNAi-inducing agents, RNAi agents, siRNAs, shRNAs, miRNAs, antisense RNAs, ribozymes, catalytic DNA, tRNA, RNAs that induce triple helix formation, aptamers, vectors, etc.). In some embodiments, the polynucleotides, primary constructs, or mmRNA may include one or more messenger RNAs (mRNAs) and one or more modified nucleoside or nucleotides (e.g., mmRNA molecules).

Design and Synthesis of mRNA

Polynucleotides, primary constructs or mmRNA for use in accordance with the invention may be prepared according to any available technique including, but not limited to chemical synthesis, enzymatic synthesis, which is generally termed in vitro transcription (IVT) or enzymatic or chemical cleavage of a longer precursor, etc. Methods of synthesizing RNAs are known in the art (see, e.g., Gait, M. J. (ed.) *Oligonucleotide synthesis: a practical approach*, Oxford [Oxfordshire], Washington, D.C.: IRL Press, 1984; and Herdewijn, P. (ed.) *Oligonucleotide synthesis: methods and applications*, Methods in Molecular Biology, v. 288 (Clifton, N.J.) Totowa, N.J.: Humana Press, 2005; both of which are incorporated herein by reference).

The process of design and synthesis of the primary constructs of the invention generally includes the steps of gene construction, mRNA production (either with or without modifications) and purification. In the enzymatic synthesis method, a target polynucleotide sequence encoding the polypeptide of interest is first selected for incorporation into a vector which will be amplified to produce a cDNA template. Optionally, the target polynucleotide sequence and/or any flanking sequences may be codon optimized. The cDNA template is then used to produce mRNA through in vitro transcription (IVT). After production, the mRNA may undergo purification and clean-up processes.

Vector Amplification

The vector containing the primary construct is then amplified and the plasmid isolated and purified using methods known in the art such as, but not limited to, a maxi prep using the Invitrogen PURELINK™ HiPure Maxiprep Kit (Carlsbad, Calif.).

Plasmid Linearization

The plasmid may then be linearized using methods known in the art such as, but not limited to, the use of restriction enzymes and buffers. The linearization reaction may be purified using methods including, for example Invitrogen's PURELINK™ PCR Micro Kit (Carlsbad, Calif.), and HPLC based purification methods such as, but not limited to, strong anion exchange HPLC, weak anion exchange HPLC, reverse phase HPLC (RP-HPLC), and hydrophobic interaction HPLC (HIC-HPLC) and Invitrogen's standard PURELINK™ PCR Kit (Carlsbad, Calif.). The purification method may be modified depending on the size of the linearization reaction which was conducted. The linearized plasmid is then used to generate cDNA for in vitro transcription (IVT) reactions.

mRNA Production

The process of mRNA or mmRNA production may include, but is not limited to, in vitro transcription, cDNA template removal and RNA clean-up, and mRNA capping and/or tailing reactions.

In Vitro Transcription

The cDNA produced in the previous step may be transcribed using an in vitro transcription (IVT) system. The system typically comprises a transcription buffer, nucleotide triphosphates (NTPs), an RNase inhibitor and a polymerase. The NTPs may be manufactured in house, may be selected from a supplier, or may be synthesized as described herein. The NTPs may be selected from, but are not limited to, those described herein including natural and unnatural (modified) NTPs. The polymerase may be selected from, but is not limited to, T7 RNA polymerase, T3 RNA polymerase and mutant polymerases such as, but not limited to, polymerases able to incorporate modified nucleic acids.

RNA Polymerases

Any number of RNA polymerases or variants may be used in the design of the primary constructs of the present invention.

RNA polymerases may be modified by inserting or deleting amino acids of the RNA polymerase sequence. As a non-limiting example, the RNA polymerase may be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants may be obtained by evolving an RNA polymerase, optimizing the RNA polymerase amino acid and/or nucleic acid sequence and/or by using other methods known in the art. As a non-limiting example, T7 RNA polymerase variants may be evolved using the continuous directed evolution system set out by Esvelt et al. (Nature (2011) 472(7344):499-503; herein incorporated by reference in its entirety) where clones of T7 RNA polymerase may encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants may encode at least mutation as described in U.S. Pub. Nos. 20100120024 and 20070117112; herein incorporated by reference in their entireties. Variants of RNA polymerase may also include, but are not limited to, substitutional variants, conservative amino acid substitution, insertional variants, deletional variants and/or covalent derivatives.

In one embodiment, the primary construct may be designed to be recognized by the wild type or variant RNA polymerases. In doing so, the primary construct may be modified to contain sites or regions of sequence changes from the wild type or parent primary construct.

In one embodiment, the primary construct may be designed to include at least one substitution and/or insertion upstream of an RNA polymerase binding or recognition site, downstream of the RNA polymerase binding or recognition site, upstream of the TATA box sequence, downstream of the TATA box sequence of the primary construct but upstream of the coding region of the primary construct, within the 5'UTR, before the 5'UTR and/or after the 5'UTR.

In one embodiment, the 5'UTR of the primary construct may be replaced by the insertion of at least one region and/or string of nucleotides of the same base. The region and/or string of nucleotides may include, but is not limited to, at least 3, at least 4, at least 5, at least 6, at least 7 or at least 8 nucleotides and the nucleotides may be natural and/or unnatural. As a non-limiting example, the group of nucleotides may include 5-8 adenine, cytosine, thymine, a string of any of the other nucleotides disclosed herein and/or combinations thereof.

In one embodiment, the 5'UTR of the primary construct may be replaced by the insertion of at least two regions and/or strings of nucleotides of two different bases such as, but not limited to, adenine, cytosine, thymine, any of the other nucleotides disclosed herein and/or combinations thereof. For example, the 5'UTR may be replaced by inserting 5-8 adenine bases followed by the insertion of 5-8 cytosine bases. In another example, the 5'UTR may be replaced by inserting 5-8 cytosine bases followed by the insertion of 5-8 adenine bases.

In one embodiment, the primary construct may include at least one substitution and/or insertion downstream of the transcription start site which may be recognized by an RNA polymerase. As a non-limiting example, at least one substitution and/or insertion may occur downstream the transcription start site by substituting at least one nucleic acid in the region just downstream of the transcription start site (such as, but not limited to, +1 to +6). Changes to region of nucleotides just downstream of the transcription start site may affect initiation rates, increase apparent nucleotide triphosphate (NTP) reaction constant values, and increase the dissociation of short transcripts from the transcription complex curing initial transcription (Brieba et al, Biochemistry (2002) 41: 5144-5149; herein incorporated by reference in its entirety). The modification, substitution and/or insertion of at least one nucleic acid may cause a silent mutation of the nucleic acid sequence or may cause a mutation in the amino acid sequence.

In one embodiment, the primary construct may include the substitution of at least 1, at least 2, at least 3, at least 4, at least 5, at least 6, at least 7, at least 8, at least 9, at least 10, at least 11, at least 12 or at least 13 guanine bases downstream of the transcription start site.

In one embodiment, the primary construct may include the substitution of at least 1, at least 2, at least 3, at least 4, at least 5 or at least 6 guanine bases in the region just downstream of the transcription start site. As a non-limiting example, if the nucleotides in the region are GGGAGA the guanine bases may be substituted by at least 1, at least 2, at least 3 or at least 4 adenine nucleotides. In another non-limiting example, if the nucleotides in the region are GGGAGA the guanine bases may be substituted by at least 1, at least 2, at least 3 or at least 4 cytosine bases. In another non-limiting example, if the nucleotides in the region are GGGAGA the guanine bases may be substituted by at least 1, at least 2, at least 3 or at least 4 thymine, and/or any of the nucleotides described herein.

In one embodiment, the primary construct may include at least one substitution and/or insertion upstream of the start codon. For the purpose of clarity, one of skill in the art would appreciate that the start codon is the first codon of the protein coding region whereas the transcription start site is the site where transcription begins. The primary construct may include, but is not limited to, at least 1, at least 2, at least 3, at least 4, at least 5, at least 6, at least 7 or at least 8 substitutions and/or insertions of nucleotide bases. The nucleotide bases may be inserted or substituted at 1, at least 1, at least 2, at least 3, at least 4 or at least 5 locations upstream of the start codon. The nucleotides inserted and/or substituted may be the same base (e.g., all A or all C or all T or all G), two different bases (e.g., A and C, A and T, or C and T), three different bases (e.g., A, C and T or A, C and T) or at least four different bases. As a non-limiting example, the guanine base upstream of the coding region in the primary construct may be substituted with adenine, cytosine, thymine, or any of the nucleotides described herein. In another non-limiting example the substitution of guanine bases in the primary construct may be designed so as to leave one guanine base in the region downstream of the transcription start site and before the start codon (see Esvelt et al. Nature (2011) 472(7344):499-503; herein incorporated by reference in its entirety). As a non-limiting example, at least 5 nucleotides may be inserted at 1 location downstream of the transcription start site but upstream of the start codon and the at least 5 nucleotides may be the same base type.

Capping and/or Tailing Reactions

The primary construct or mmRNA may also undergo capping and/or tailing reactions. A capping reaction may be performed by methods known in the art to add a 5' cap to the 5' end of the primary construct. Methods for capping include, but are not limited to, using a Vaccinia Capping enzyme (New England Biolabs, Ipswich, Mass.).

A poly-A tailing reaction may be performed by methods known in the art, such as, but not limited to, 2' O-methyltransferase and by methods as described herein. If the primary construct generated from cDNA does not include a poly-T, it may be beneficial to perform the poly-A-tailing reaction before the primary construct is cleaned.

mRNA Characterization

Primary construct or mmRNA purification may include, but is not limited to, mRNA or mmRNA clean-up, quality assurance and quality control. mRNA or mmRNA clean-up may be performed by methods known in the arts such as, but not limited to, AGENCOURT® beads (Beckman Coulter Genomics, Danvers, Mass.), poly-T beads, LNATM oligo-T capture probes (EXIQON® Inc, Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC). The term "purified" when used in relation to a polynucleotide such as a "purified mRNA or mmRNA" refers to one that is separated from at least one contaminant. As used herein, a "contaminant" is any substance which makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

A quality assurance and/or quality control check may be conducted using methods such as, but not limited to, gel electrophoresis, UV absorbance, or analytical HPLC.

In another embodiment, the mRNA or mmRNA may be sequenced by methods including, but not limited to reverse-transcriptase-PCR.

In one embodiment, the mRNA or mmRNA may be quantified using methods such as, but not limited to, ultraviolet visible spectroscopy (UV/Vis). A non-limiting example of a UV/Vis spectrometer is a NANODROP® spectrometer (ThermoFisher, Waltham, Mass.). The quantified mRNA or mmRNA may be analyzed in order to determine if the mRNA or mmRNA may be of proper size, check that no degradation of the mRNA or mmRNA has occurred. Degradation of the mRNA and/or mmRNA may be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

cDNA Template Removal and Clean-Up

There are several commonly used methods to achieve partial or near complete removal of DNA from mRNA at different scales. These methods are based on the differences in molecular structures or biochemical properties of DNA and RNA. For example, DNase I digestion uses the enzymatic substrate specificity to selectively cleave DNA molecules but leave RNA molecules intact and organic solvent extraction is based on the differential partitioning of DNA and RNA into organic and aqueous phases.

DNase I is an endonuclease that cleaves DNA by breaking phosphodiester bonds and produces smaller DNA fragments and/or di-, tri- and oligonucleotides which are subsequently removed by size-based separation methods. However, it is challenging to quantitatively determine the DNase I digestion efficiency and DNase I itself requires to be inactivated or removed in the subsequent process. Quantitative PCR is often applied to measure the residual DNA but it only detects the DNA molecules that contain both qPCR primers thus does not measure all other smaller DNA molecules that are partially digested. To overcome this challenge, a liquid chromatography-tandem mass spectrometry (LC/MS/MS) approach can be used where a total nuclease digestion is performed on the RNA drug substance sample following the DNA removal step. The presence of individual residual deoxynucleotides is quantitatively assayed against deoxynucleotide standards using MS/MS and the abundance is reported.

The cDNA template may be removed using methods known in the art such as, but not limited to, treatment with Deoxyribonuclease I (DNase I). RNA clean-up may also include a purification method such as, but not limited to, AGENCOURT® CLEANSEQ® system from Beckman Coulter (Danvers, Mass.), HPLC based purification methods such as, but not limited to, strong anion exchange HPLC, weak anion exchange HPLC, reverse phase HPLC (RP-HPLC), and hydrophobic interaction HPLC (HIC-HPLC).

DNase Treatment

To remove a DNA template from an in vitro transcription product, a portion of the transcription product can be incubated with DNase, for example DNase I. Then, the RNA transcript is separated from the digested DNA template by a separation method. For example, the separation method could be centrifugation, ultrafiltration, a precipitation, liquid chromatography, gel electrophoresis, or use of a vacuum column.

In some embodiments, a portion of the digested in vitro transcription product can be incubated with a second nuclease (for example, nuclease P1) for further analysis by liquid chromatography-tandem mass spectrometry (LC/MS/MS), where the presence or absence of residual deoxynucleotides in the digested product is detected. The total abundance of deoxynucleotides present in the RNA sample via the mass spectrometry analysis can be, for example, <500 ppm, <300 ppm, <250 ppm, <100 ppm, <50 ppm, <25 ppm, <10 ppm, <5 ppm, <1 ppm, or <0.2 ppm.

In another embodiment, the DNase could be attached to a solid support, such as a solid phase resin, controlled pore glass, polystyrene, polystyrene divinyl benzene, cellulose, polyacrylamide, silica, polymethacrylate, or dextran based polymers. The in vitro transcription reaction product can be contacted with the solid support to digest the DNA template.

Removal of Labeled DNA

In some embodiments, the DNA template is coupled to a label, so that the labeled DNA can later be separated from the RNA transcript in an in vitro transcription reaction product by running the product on a solid support that presents a ligand or functional group configured to bind the label.

In one embodiment, the DNA template is a plasmid is coupled to the label either before or after the plasmid has been linearized, where the plasmid has been linearized with a restriction enzyme.

In another embodiment, the DNA template is a PCR product. In a further embodiment one or more of the PCR primers is labeled, so that during the PCR amplification, the label will become coupled to the DNA template amplicon. In a further embodiment, the PCR primers are chemically synthesized. In a separate embodiment, the label is coupled to the 5'-end of the DNA template. The label can be a reactive group, such as a biotin, an amine, or a thiol. Biotin could be coupled to the DNA template by an alkylation reaction, whereas the amine could be coupled by heat activation or light activation.

In a separate embodiment, the DNA template is a PCR product, where the label is coupled to the DNA template by a DNA polymerase. For example, the label can be made up of modified nucleotides, so the DNA template could be made of these modified nucleotide labels. For example, the modified nucleotides could be 5' aminoallyl pyrimidine NTPs, or N-6-aminohexyl cytidine NTPs. Furthermore, the modified nucleotides could comprise nucleotide analogs coupled to an intrinsic linker.

After the in vitro transcription reaction, the reaction product containing the labeled DNA template can be run on a solid support, where the solid support is configured to bind the label. A biotinylated DNA template will bind a streptavidin resin, an amine labeled DNA template will bind a N-hydroxysuccinimide-activated resin, and a DNA labeled with modified nucleotide aminoallyl-dUTP will be removed by reactive forms of cyanine 3 or cyanine 5—NHS esters (for example, using the Illustra CyScribe GFX Purification Kit from GE Healthcare). Also, epoxide or aldehyde resins may be used.

EXAMPLES

Example 1: Preparing Plasmids for cDNA Production cDNA is produced to provide a DNA template for in vitro transcription. To prepare plasmids for producing cDNA, NEB DH5-alpha Competent *E. coli* are used in one example. Transformations are performed according to NEB instructions using 100 ng of plasmid. The protocol is as follows:

Spread 50-100 µl of each dilution onto a selection plate and incubate overnight at 37° C. Alternatively, incubate at 30° C. for 24-36 hours or 25° C. for 48 hours.

A single colony is then used to inoculate 5 ml of LB growth media using the appropriate antibiotic and then allowed to grow (250 RPM, 37° C.) for 5 hours. This is then used to inoculate a 200 ml culture medium and allowed to grow overnight under the same conditions.

To isolate the plasmid (up to 850 µg), a maxi prep is performed using the Invitrogen PURELINK™ HiPure Maxiprep Kit (Carlsbad, Calif.), following the manufacturer's instructions, which are as follows: thaw a tube of NEB 5-alpha Competent *E. coli* cells on ice for 10 minutes. Add 1-5 µl containing 1 pg-100 ng of plasmid DNA to the cell mixture. Carefully flick the tube 4-5 times to mix cells and DNA. Do not vortex. Place the mixture on ice for 30 minutes. Do not mix. Heat shock at 42° C. for 30 seconds. Do not mix. Place on ice for 5 minutes. Do not mix. Pipette 950 µl of room temperature SOC into the mixture. Place at 37° C. for 60 minutes. Shake vigorously (250 rpm) or rotate. Warm selection plates to 37° C. Mix the cells thoroughly by flicking the tube and inverting.

In order to generate cDNA for In vitro Transcription (IVT), the plasmid is first linearized using a restriction enzyme such as XbaI. A typical restriction digest with XbaI will comprise the following: Plasmid 1.0 µg; 10× Buffer 1.0 µl; XbaI 1.5 µl; dH20 up to 10 µl; incubated at 37° C. for 1 hr. If performing at lab scale (<5 μg), the reaction is cleaned up using Invitrogen's PURELINK™ PCR Micro Kit (Carlsbad, Calif.) per manufacturer's instructions. Larger scale purifications may need to be done with a product that has a larger load capacity such as Invitrogen's standard PURELINK™ PCR Kit (Carlsbad, Calif.). Following the cleanup, the linearized vector is quantified using the Nano-Drop and analyzed to confirm linearization using agarose gel electrophoresis.

Example 2: PCR for cDNA Production

PCR procedures for the preparation of cDNA are performed using 2× KAPA HIFI™ HotStart ReadyMix by Kapa Biosystems (Woburn, Mass.). This system includes 2× KAPA ReadyMix 12.5 μl; Forward Primer (10 uM) 0.75 μl; Reverse Primer (10 uM) 0.75 μl; Template cDNA 100 ng; and dH20 diluted to 25.0 μl. The reaction conditions are at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention incorporates a poly-T120 for a poly-A120 in the mRNA. Other reverse primers with longer or shorter poly(T) tracts can be used to adjust the length of the poly(A) tail in the mRNA.

The reaction is cleaned up using Invitrogen's PURELINK™ PCR Micro Kit (Carlsbad, Calif.) per manufacturer's instructions (up to 5 μg). Larger reactions will require a cleanup using a product with a larger capacity. Following the cleanup, the cDNA is quantified using the NANODROP™ and analyzed by agarose gel electrophoresis to confirm the cDNA is the expected size. The cDNA is then submitted for sequencing analysis before proceeding to the in vitro transcription reaction.

Example 3: In Vitro Transcription (IVT)

mRNAs according to the invention may be made using standard laboratory methods and materials. The open reading frame (ORF) of the gene of interest may be flanked by a 5' untranslated region (UTR), which may contain a strong Kozak translational initiation signal and/or an alpha-globin 3' UTR which may include an oligo(dT) sequence for templated addition of a poly-A tail. The mRNAs may be modified to reduce the cellular innate immune response. The modifications to reduce the cellular response may include pseudouridine (ψ) and 5-methyl-cytidine (5meC, 5mc or m5C). (See Kariko K et al. Immunity 23:165-75 (2005), Kariko K et al. Mol Ther 16:1833-40 (2008), Anderson B R et al. NAR (2010); each of which are herein incorporated by reference in their entireties).

The ORF may also include various upstream or downstream additions (such as, but not limited to, β-globin, tags, etc.) may be ordered from an optimization service such as, but limited to, DNA2.0 (Menlo Park, Calif.) and may contain multiple cloning sites which may have XbaI recognition. Upon receipt of the construct, it may be reconstituted and transformed into chemically competent E. coli.

The in vitro transcription reaction can generate mRNA containing modified nucleotides or modified RNA. The input nucleotide triphosphate (NTP) mix is made in-house using natural and un-natural NTPs.

A typical in vitro transcription reaction includes the following:

| 1 | Template cDNA | 1.0 μg |
| --- | --- | --- |
| 2 | 10× transcription buffer (400 mM Tris-HCl pH 8.0, 190 mM MgCl$_2$, 50 mM DTT, 10 mM Spermidine) | 2.0 μl |
| 3 | Custom NTPs (25 mM each) | 7.2 μl |
| 4 | RNase Inhibitor | 20 U |
| 5 | T7 RNA polymerase | 3000 U |
| 6 | dH$_2$0 | Up to 20.0 μl. and |
| 7 | Incubation at 37° C. for 3 hr-5 hrs. | |

The crude IVT mix may be stored at 4° C. overnight for cleanup the next day. 1 U of RNase-free DNase is then used to digest the original template. After 15 minutes of incubation at 37° C., the mRNA is purified using Ambion's MEGACLEAR™ Kit (Austin, Tex.) following the manufacturer's instructions. This kit can purify up to 500 μg of RNA. Following the cleanup, the RNA is quantified using the NanoDrop and analyzed by agarose gel electrophoresis to confirm the RNA is the proper size and that no degradation of the RNA has occurred.

Example 4: Removal of DNA Template from IVT Product Using DNase

Following the in vitro transcription process, the DNA template was removed to isolate the RNA transcript. Several different methods have been used to remove the DNA, including incubation with DNase enzyme.

DNase I: For each μg of DNA template (either a PCR product or a linearized plasmid), 2 Units of DNase I enzyme were added to the in vitro transcription product. Upon completion of the in vitro transcription reaction, the entire sample was incubated for 1 hour at 37° C. Next, the digested DNA fragments or single deoxynucleotides were removed from the sample by ultrafiltration through centrifugation, leaving the isolated RNA transcript. Quantitation of the residual deoxynucleotides was performed by liquid chromatography-tandem mass spectrometry analysis.

DNase I solid phase resin: Alternatively, the in vitro transcription reaction product is applied to a solid phase resin containing immobilized DNase I. This preferred method is used because no enzyme contamination is added to the in vitro transcription mix. Columns containing immobile DNase I on a resin is purchased from Boca Scientific, Inc. (Boca Raton, Fla.). The in vitro transcription reaction product is added to the resin, and the RNA transcript is recovered from the resin.

Example 5: Removal of DNA Template from IVT Product Using Labeled DNA

Alternative to incubating the in vitro transcription product with DNase enzyme, labeled DNA transcripts are used to remove DNA from an in vitro transcription product to isolate the RNA transcript. The DNA template is synthesized to contain one a label (tag) to be used in post IVT removal of DNA. The proposed solid phase-based removal methods are effective for both linearized plasmid DNA or PCR amplified DNA. The labels/tags are selected based on their reactive chemical properties such that the labeled DNA is bound to proper solid resin that has high specific affinity for the chemical label/tag.

Plasmid DNA as template: if the DNA template is a plasmid, the plasmid may be labeled before or after linearization of the plasmid with a restriction enzyme. The LabeIIT® Tracker™ Intracellular Nucleic Acid Localization Kit (Mirus Bio, LLC) is used to couple a biotin molecule to the DNA template plasmid via DNA alkylation. The labeling reaction targets random sites on the DNA template, whereby each biotin molecule is covalently attached to one DNA template plasmid molecule. This non-destructive labeling reaction has produced mRNA functional in gene expression assay according to a statement of the manufacturer. A sufficient number of DNA template plasmid molecules are labeled at sites that are not involved in transcription, such that the DNA is effectively labeled without interfering with the in vitro transcription reaction.

If biotin is not used to label the DNA template, the plasmid DNA can be labeled with an amine. For example, PHOTOPROBE® (Vector Laboratories, Inc.) is a photo-activated labeling reagent that covalently couples an amino group to the DNA template. After adding PHOTOPROBE® to the DNA template sample, the labeling reaction is initiated by heat or light exposure (365 nm). Again, the labeling reaction targets random sites on the DNA template, but a sufficient number of DNA template plasmid molecules are amino-labeled at sites that are not involved in transcription, so the DNA is labeled without interfering with the in vitro transcription reaction.

PCR amplified DNA as template: Another method of labeling the DNA template includes labeling the DNA during PCR. The primers for use in the PCR are chemically synthesized, and a biotin, amine, thiol, or other label is added to the end of one or more of the primers. A large batch of labeled primers is manufactured and used in a PCR that amplifies the DNA template. When the PCR is complete, the DNA template has been amplified and is coupled to the label. Also, a labeled plasmid as discussed above can be used as a DNA template to produced labeled amplified DNA template molecules.

Alternative to labeling PCR primers or using an already-labeled DNA template, modified nucleotides such as 5-aminoallyl pyrimidine NTPs or N-6-aminohexyl cytidine NTPs are used to label the DNA template. The ideal ration of one modified nucleotide per DNA molecule is achievable by titration of the concentration of modified nucleotide to that of natural nucleotides. The degree of incorporation is not critical as any DNA containing more than 1 target affinity ligand will also be captured. Likewise, the impact of labeling on transcription remains to be determined. During the PCR, DNA polymerase amplifies the DNA template using the modified nucleotides, so that after completion of PCR, the amplified DNA template contains modified nucleotides. In another example, a PCR reaction is performed to produce cDNA fragments first, then apply plasmid labeling technique to PCR amplified DNA with biotin using the method described above (Mirus LabelIT® Tracker™ Intracellular Nucleic Acid Localization KitA). PCR amplified DNA template produced by any of the aforementioned methods can now be used in an in vitro transcription reaction to produce an RNA transcript.

Removal of DNA template: After in vitro transcription produces an RNA transcript sample from a DNA template, the DNA is removed from the sample by contacting the sample with a resin designed to bind the label. For example, if the DNA template is labeled with biotin, a streptavidin resin is used. If the DNA is labeled with nucleotide analog aminoallyl-dUTP, reactive forms of cyanine 3 or cyanine 5-NHS esters are used (for example, Illustra CyScribe GFX Purification Kit, GE Healthcare). If the DNA template is labeled with an amine, an NHS activated resin is used. In many cases, experimental evidence is required to identify the optimal tag. Post-in vitro transcription purification methods are developed individually for each label. However, these are standard interactions widely used in industrial applications. The labeled DNA is retained on the resin, and the isolated RNA transcript is recovered.

In all the above cases, the labeled DNA will be retained on resin and mRNA should be conveniently recovered in the flow-through for downstream processes. Again, the efficiency of cDNA removal will be assayed by LC/MS/MS analysis.

The new methods are superior to previous practice in that no DNase I enzyme is required, and the purification/DNA removal process is done by a single step column. It can be conveniently scaled up for larger batches. The mRNA should be recovered with high yield and not suffer additional loss as in other purification or partitioning methods. If labeled cDNA is removed without enzyme digestion, there are no concerns of secondary contamination of smaller DNA fragments or oligonucleotides.

Example 6: Quantitation of RNA Transcript for Detection of Impurities

After removal of the DNA (either by DNase digestion or removal of labeled DNA), the RNA transcript sample is subjected to a total nuclease digestion using nuclease P1. Thus, the presence of any deoxythymidine (dT), deoxyadenine (dA), deoxycytidine (dC), and deoxyguanosine (dG) are detected and their levels quantified by LC-MS/MS.

Then, the sample is subjected to liquid chromatography-tandem mass spectrometry analysis to detect the presence of individual residual deoxynucleotides (impurities).

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES CITED

FDA Regulatory guidance for residual DNA http://www.fda.gov/downloads/biologicsbloodvaccines/guidancecompli-anceregulatoryinformation/guidances/vaccines/ucm202439.pdf

What is claimed is:

1. A method for removing a DNA template from a sample comprising the DNA template and an RNA transcript, comprising:
    (a) obtaining the sample;
    (b) digesting the DNA template by contacting the sample with a DNase enzyme to produce a sample comprising digested DNA template and the RNA transcript;
    (c) contacting a portion of the sample of step (b) with a second nuclease under conditions that promote nucleotide digestion to obtain a digested sample;
    (d) analyzing the digested sample by liquid chromatography-tandem mass spectrometry; and
    (e) detecting the presence or absence of residual deoxynucleotides in the digested product based on the liquid chromatography-tandem mass spectrometry analysis; and
    (f) separating the digested DNA template from the RNA transcript by a process that comprises centrifugation and ultrafiltration.

2. The method of claim 1, wherein the RNA transcript is the product of in vitro transcription using a non-amplified DNA template.

3. The method of claim 1, wherein the RNA transcript is a full length RNA transcript.

4. The method of claim 1, wherein the RNA transcript comprises chemically modified mRNA molecules.

5. The method of claim 1, wherein the RNA transcript is between 100 and 10,000 nucleotides in length.

6. The method of claim 1, wherein the process of step (f) further comprises a precipitation, liquid chromatography, a gel electrophoresis, or a vacuum.

7. The method of claim 1, wherein the DNase is DNase I.

8. The method of claim 7, wherein 2 units of DNase I are added for each µg of DNA template in the sample.

9. The method of claim 7, wherein the DNase I is incubated with the sample at 37° C. for one hour.

10. The method of claim 1, wherein the DNase is attached to a solid support.

11. The method of claim 10, wherein the solid support is a solid phase resin, controlled pore glass, polystyrene, polystyrene divinyl benzene, cellulose, polacrylamide, silica, polymethacrylate, or a dextran based polymer.

* * * * *

SEQUENCE LISTING

<160> NUMBER OF SEQ ID NOS: 3

<210> SEQ ID NO 1
<211> LENGTH: 300
<212> TYPE: DNA

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(300)
<223> OTHER INFORMATION: This sequence may encompass 5-300 nucleotides,
      wherein some positions may be absent

<400> SEQUENCE: 1
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300

<210> SEQ ID NO 2
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120

<210> SEQ ID NO 3
<211> LENGTH: 120
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
tttttttttt tttttttttt tttttttttt tttttttttt tttttttttt tttttttttt      60
tttttttttt tttttttttt tttttttttt tttttttttt tttttttttt tttttttttt     120
```